(12) United States Patent
Liphardt et al.

(10) Patent No.: US 6,950,182 B1
(45) Date of Patent: Sep. 27, 2005

(54) FUNCTIONAL EQUIVALENT TO SPATIAL FILTER IN ELLIPSOMETER AND THE LIKE SYSTEMS

(75) Inventors: Martin M Liphardt, Lincoln, NE (US); Blaine D. Johs, Lincoln, NE (US); Craig M. Herzinger, Lincoln, NE (US); Ping He, Lincoln, NE (US)

(73) Assignee: J. A. Woollam Co., Lincoln, NE (US)

( * ) Notice: Subject to any disclaimer, the term of this patent is extended or adjusted under 35 U.S.C. 154(b) by 506 days.

(21) Appl. No.: 10/178,723

(22) Filed: Jun. 24, 2002

Related U.S. Application Data

(63) Continuation-in-part of application No. 09/864,840, filed on May 24, 2001, now Pat. No. 6,456,376, and a continuation-in-part of application No. 09/845,548, filed on Apr. 30, 2001, now Pat. No. 6,585,128, and a continuation-in-part of application No. 09/419,794, filed on Oct. 18, 1999, now Pat. No. 6,549,282.

(60) Provisional application No. 60/300,714, filed on Jun. 26, 2001.

(51) Int. Cl.[7] ............................. G01N 21/00; G01J 4/00
(52) U.S. Cl. ..................................... 356/237.1; 356/369
(58) Field of Search .................. 356/237.1–237.5, 356/364–369; 250/559.4, 559.41, 559.45

(56) References Cited

U.S. PATENT DOCUMENTS

| | | | | |
|---|---|---|---|---|
| 3,782,827 A | * | 1/1974 | Nisenson et al. | 356/600 |
| 3,905,675 A | | 9/1975 | McCracker | 350/17 |
| 4,636,075 A | | 1/1987 | Knollenberg | 356/336 |
| 4,668,860 A | | 5/1987 | Anthon | 250/225 |
| RE32,660 E | * | 5/1988 | Lindow et al. | 250/225 |
| 4,877,960 A | | 10/1989 | Messerschmidt et al. | 250/341 |
| 4,893,932 A | | 1/1990 | Knollenberg | 356/369 |
| 5,148,323 A | | 9/1992 | Campbell et al. | 359/738 |
| 5,333,052 A | | 7/1994 | Finarov | 356/369 |
| 5,517,312 A | | 5/1996 | Finarov | 356/386 |
| 5,608,526 A | | 3/1997 | Piwonka-Corle et al. | 356/369 |
| 5,684,642 A | | 11/1997 | Zumoto et al. | 359/40 |
| 5,793,480 A | | 8/1998 | Lacey et al. | 356/73 |
| 5,798,837 A | | 8/1998 | Aspnes et al. | 356/369 |
| 5,859,424 A | * | 1/1999 | Norton et al. | 250/226 |
| 5,859,705 A | * | 1/1999 | Benedetto et al. | 356/336 |
| 5,877,859 A | | 3/1999 | Aspnes et al. | 356/364 |
| 5,917,594 A | | 6/1999 | Norton | 356/327 |
| 6,084,671 A | * | 7/2000 | Holcomb | 356/511 |
| 6,208,418 B1 | * | 3/2001 | Maris | 356/388 |
| 6,545,764 B1 | * | 4/2003 | Laczik | 356/601 |
| 6,618,134 B2 | * | 9/2003 | Vaez-Iravani et al. | 356/237.4 |
| 2004/0212807 A1 | * | 10/2004 | Hanson et al. | 356/458 |

OTHER PUBLICATIONS

"Regression Calibration Method for Rotating Element Ellipsometers", Johs, Thin Solid Films, 234 (1993).
"Systematic and Random Errors in Rotating-Analyzer Ellipsometry", Nijs & Silfhout, J. Opt. Soc. Am., vol. 5, No. 6, (Jun. 1988).

(Continued)

*Primary Examiner*—Hoa Q. Pham
(74) *Attorney, Agent, or Firm*—James D. Welch

(57) ABSTRACT

Disclosed is the application of a functional equivalent to a spatial filter in ellipsometer and the like systems. Included are demonstrated multi-element converging lens systems which focus an electromagnetic beam onto a fiber optic. The purpose is to eliminate a radially outer annulus of a generally arbitrary intensity profile, so that electromagnetic beam intensity is caused to quickly decay to zero, rather than, for instance, demonstrate an irregular profile as a function of radius.

7 Claims, 8 Drawing Sheets

OTHER PUBLICATIONS

"Systematic Errors in Rotating-Compensator ellipsometry", Kleim et a., lJ. Opt. Soc. Am., vol. 11 No. 9, (setp. 1994).

"Unified Analysis of Ellipsometry Errors Due to Imperfect Components Cell-Window Birefringence, an Incorrect Azimuth Angles", Azzam & Bashara, J. of the Opt. Soc. Am., vol. 61, No. 5, (May 1971).

"Analysis of Systematic Errors in Rotating-Analyzer Ellipsometers", Azzam & Bashara, J. of the Opt. Soc. Am., vol. 64, No. 11, (Nov. 1974).

"The Influence of Cell Window Imperfections on the Calibration and Measured Data of Two Types of Rotating Analyzer Ellipsometers", Straaher et alSurface Sci., North Holland, 96, (1980).

"A New Calculus For The Treatment Of Optical Systems", Jines, J.O.S.A., vol. 31, (Jul. 1941), is also indentified as it describes the characterizing of multiple lens elements which seperately demonstrate birefringence, as a single lens, (which can demonstrate reduced birefringence).

"In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., vol. 406, (1996) is also disclosed.

* cited by examiner

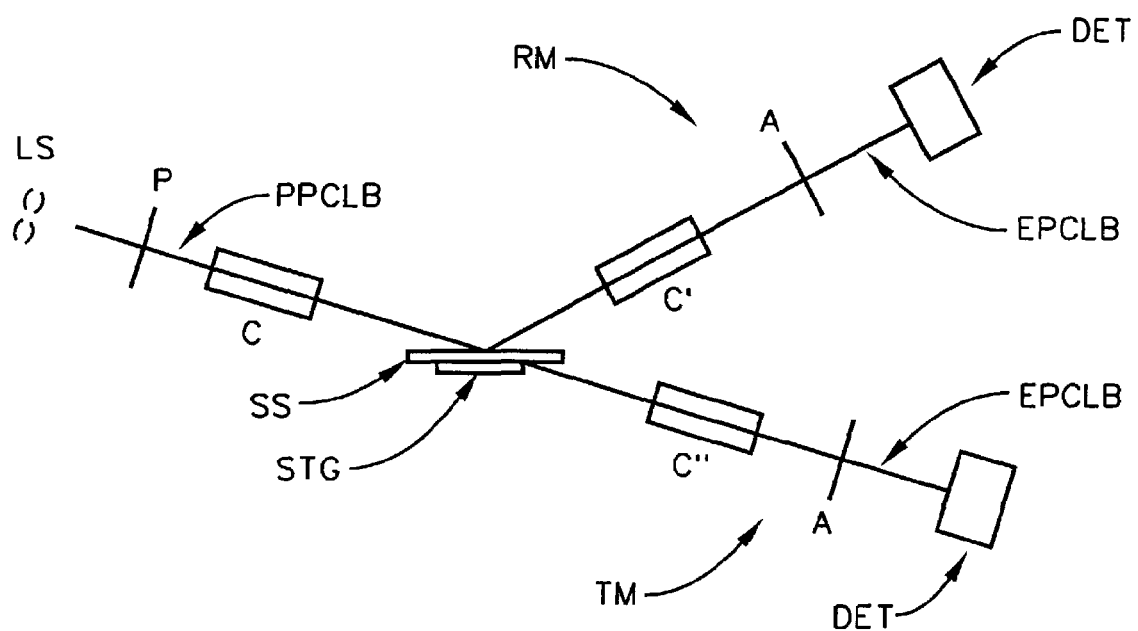
FIG. 1a₁
PRIOR ART
FIG. 1b₁
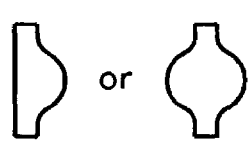
FIG. 1b₃
FIG. 1b₂
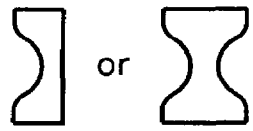
FIG. 1b₄

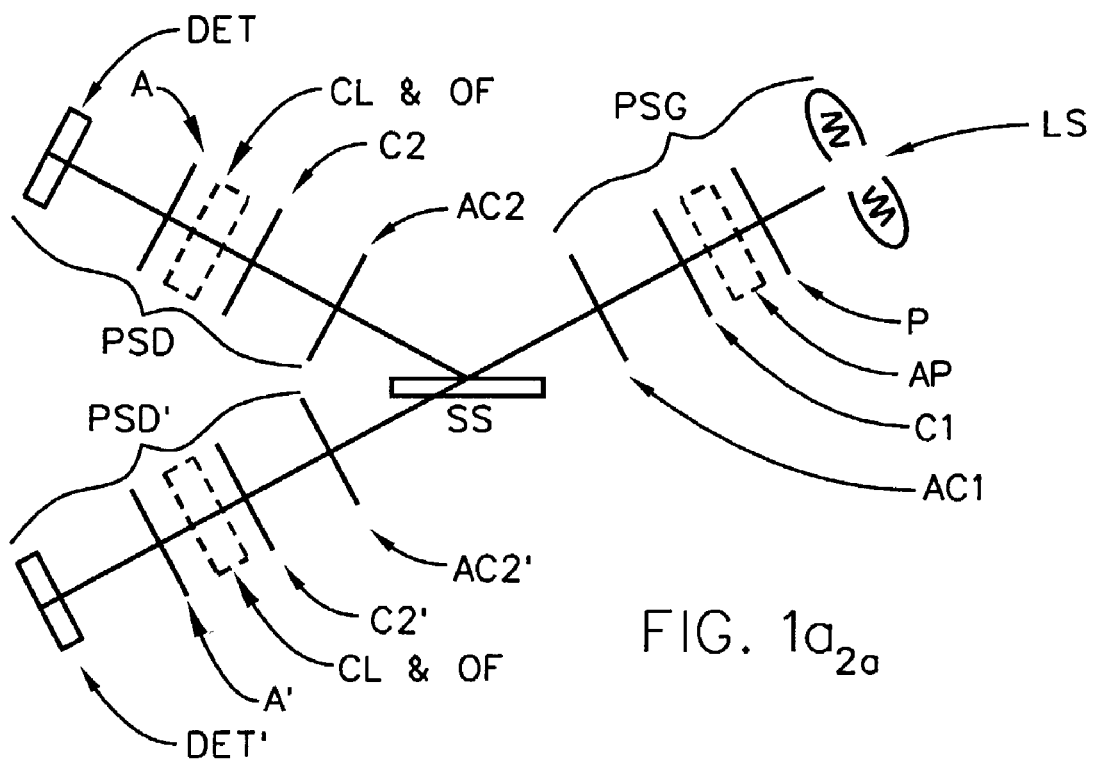
FIG. $1a_{2a}$
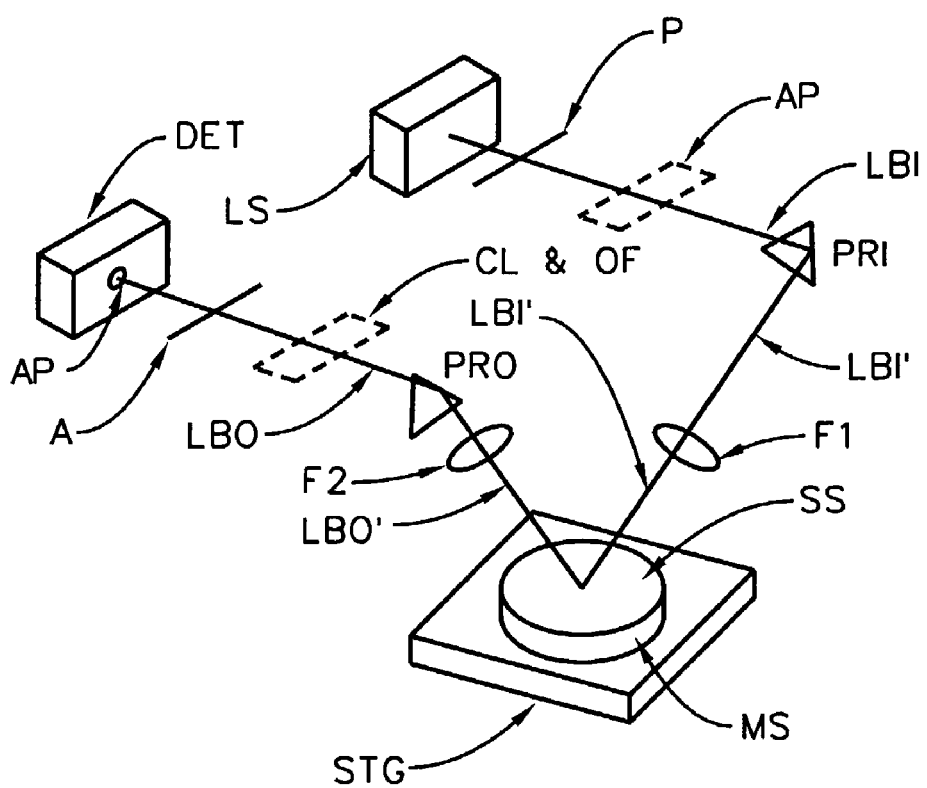
FIG. $1a_{2b}$

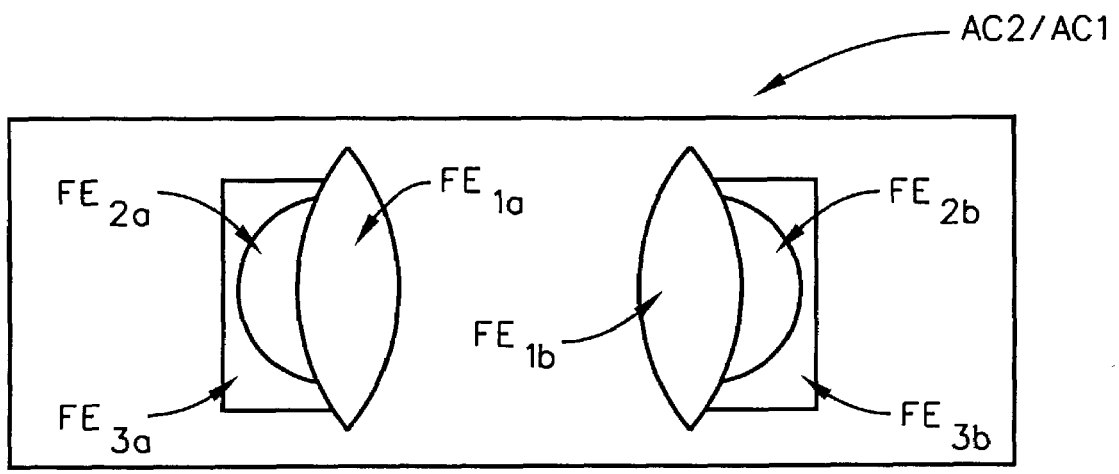
FIG. $1a_4$
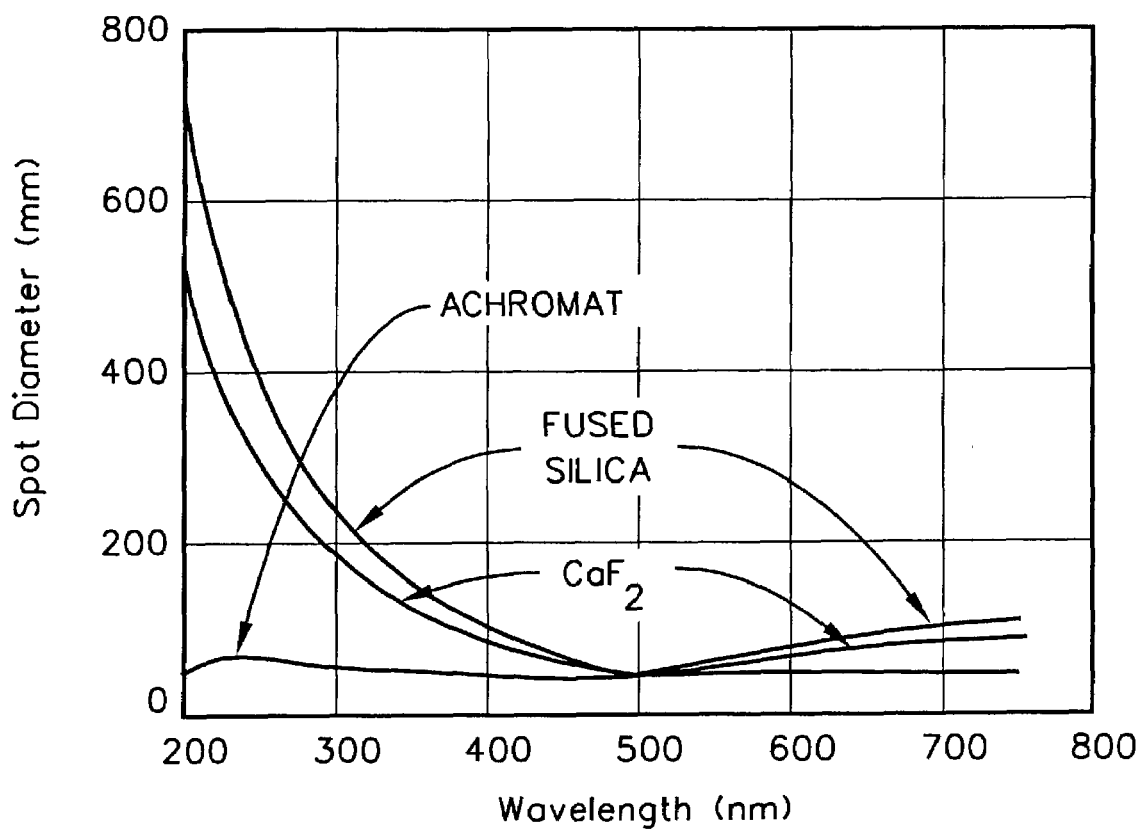
FIG. $1a_5$

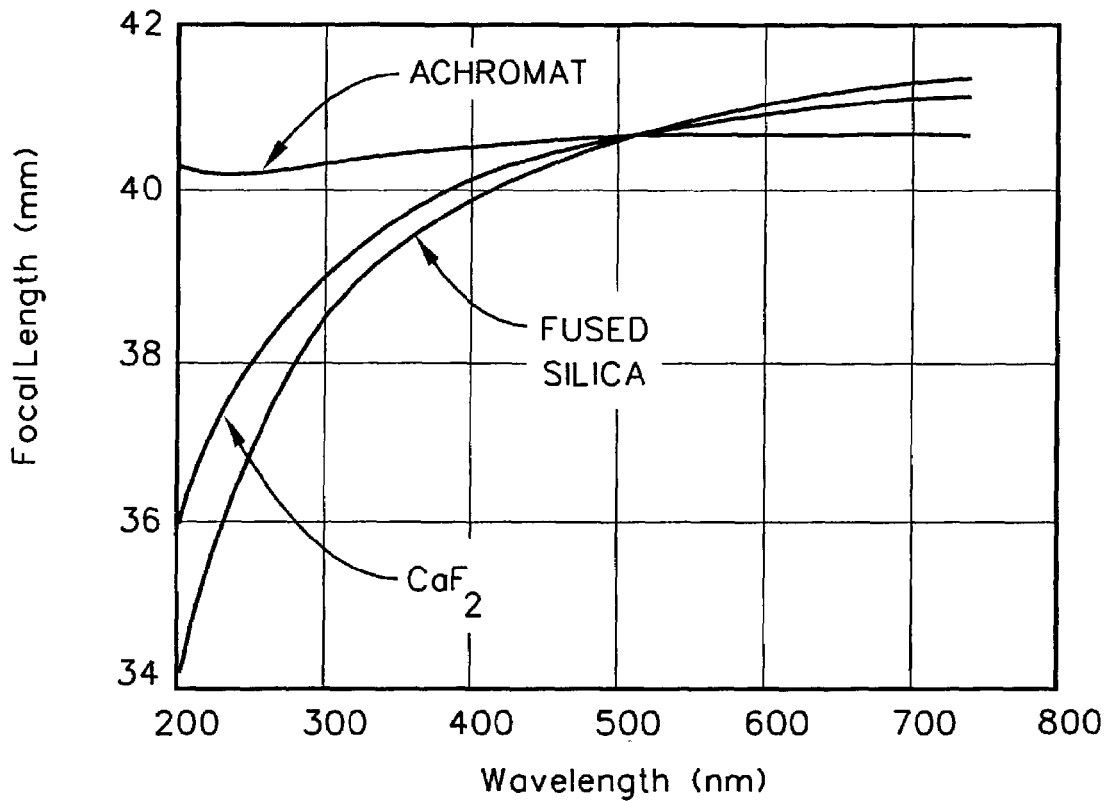
FIG. $1a_6$
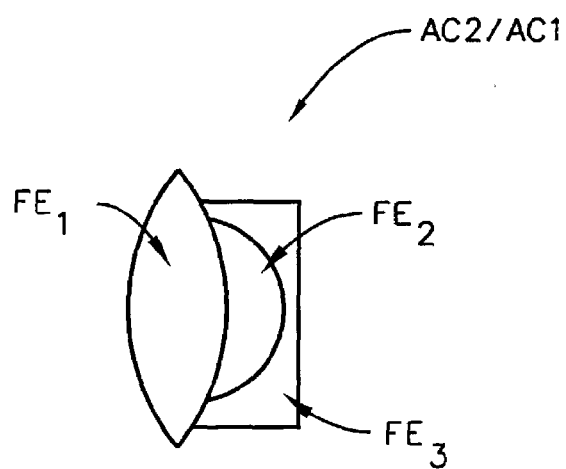
FIG. $1a_3$

FUNCTIONAL EQUIVALENT TO SPATIAL FILTER IN ELLIPSOMETER AND THE LIKE SYSTEMS

This Application is a CIP of applications Ser. Nos.:
09/864,840 Filed May 24, 2001, (now U.S. Pat. No. 6,456,376);
09/419,794 Filed Oct. 18, 1999, (now U.S. Pat. No. 6,549,282);
09/845,548 Filed Apr. 30, 2001, now U.S. Pat. No. 6,585,128;

and claims Benefit of Provisional Application Ser. No. 60/300,714, Filed Jun. 26, 2001.

TECHNICAL FIELD

The present invention relates to conditioning electromagnetic beams in ellipsometer and the like systems, and more particularly to a system for providing the functional equivalent to spatial filtering therein.

BACKGROUND

Not limited to, but particularly in the case where an electromagnetic beam is utilized to investigate a sample system which presents with a varying depth surface topology, it is important to provide an electromagnetic beam of a known lateral dimension and which presents with a relatively simple cross-sectional Intensity profile.

It is noted that often electromagnetic beams present with a substantially arbitrary intensity profile, with the highest intensity generally being located centrally, and with intensity decreasing with increasing radius. While such a beam intensity profile is typically acceptable for use in ellipsometry and related practices, it has been found that once the intensity of a substantially arbitrary profile beam of electromagnetic radiation has dropped to, as an arbitrary example, say ten (10%) of its maximum, that said intensity in many beams does not, always continue to decay directly to essentially zero (0.0). Instead, it often presents irregularly as a function of radius, (eg. easily visualized as being generally similar to the Fourier transform of a square wave). The cause of said irregular intensity profile can include such as optical element wavelength dependent diffraction, surface roughness or other non-idealities, and where, for instance, electromagnetic radiation is provided via an aperture or via the end of a light fiber contained in a cladding, such that electromagnetic radiation falls outside a geometric image thereof.

It would be of benefit, as regards obtaining accurate data from application of ellipsometers and the like systems, if the intensity of an electromagnetic beam could be forced to decay quickly to zero (0.0), rather than demonstrate an irregular intensity profile as a function of radius.

With an eye to the present invention, a Search of Patents was conducted. Perhaps the most relevant Patent identified is U.S. Pat. No. 5,517,312 to Finarov. Said 312 Patent describes application of a scattered light reducing system at the entry to a Detector of an Ellipsometer or Spectrophotometer System, which scattered light reducing system consists of two lenses with a pin-hole containing diaphram located midway therebetween, and at the focal lengths of said lenses. Said scattered light reducing system is present after a sample system and processes electromagnetic radiation after it interacts with said sample system. The pinhole is described as serving to provide high spatial resolution as well as reduce scattered light. Another Patent identified is that to Campbell et al., U.S. Pat. No. 5,148,323. Said 323 Patent describes a Spatial Filter in which a pinhole is located other than at the focal length of a converging lens. U.S. Pat. No. 3,905,675 to McCraken describes a Spatial Filter containing system which enables observation of a weak source of electromagnetic radiation in the presence of strong sources thereof. U.S. Pat. No. 5,684,642 to Zumoto et al., describes an optical transmission system for use in fashioning an electromagnetic beam for use in machining materials which combines a Spatial Filter and an Optical Fiber. U.S. Pat. No. 4,877,960 is identified as it describes masking energy from outside the target area of a in a microscope having dual remote image masking.

Patents identified in a Search specifically focused on the use of lenses, preferably achromatic, in ellipsometry and related systems are:
U.S. Pat. Nos. 5,877,859 and 5,798,837 to Aspnes et al.;
U.S. Pat. No. 5,333,052 to Finarov;
U.S. Pat. No. 5,608,526 to Piwonka-Corle et al.;
U.S. Pat. No. 5,793,480 to Lacy et al.;
U.S. Pat. Nos. 4,636,075 and 4,893,932 to Knollenberg; and
U.S. Pat. No. 4,668,860 to Anthon.

The most relevant Patent found is U.S. Pat. No. 5,917,594 to Norton. However, the system disclosed therein utilizes a spherical mirror to focus an electromagnetic beam onto the surface of a sample in the form of a small spot. Said system further develops both reflection and transmission signals via application of reflective means and of reflection and transmission detectors. The somewhat relevant aspect of the 594 Patent system is that a positive lens and a negative meniscus lens are combined and placed into the pathway of the electromagnetic beam prior to its reflection from a focusing spherical mirror. The purpose of doing so is to make the optical system, as a whole, essentially achromatic in the visible wavelength range, and even into the ultraviolet wavelength range. It is further stated that the power of the combined positive lens and negative meniscus lens is preferably zero. It is noted that, as described elsewhere in this Specification, said 594 Patent lens structure, positioning in the 594 Patent system, and purpose thereof are quite distinct from the present invention lens structure and application to focus a beam of electromagnetic radiation. In particular, note that the 594 Patent lens is not applied to directly focus and/or recollimate a beam of electromagnetic radiation onto a sample system, as do the lenses in the present invention. And, while the present invention could utilize a meniscus lens in an embodiment thereof, the 594 Patent specifically requires and employs a negative meniscus lens to correct for spherical aberrations caused by off-axis reflection from a spherical mirror, in combination with a positive lens to correct for achromatic aberration introduced by said negative meniscus lens. Further, the present invention system does not require reflection means be present in the path of an electromagnetic beam after its passage through the focusing lens thereof and prior to interacting with a sample system, as does the system in the 594 Patent wherein a focusing spherical mirror is functionally required.

Various papers were also identified as possibly pertinent, and are:
A paper by Johs, titled "Regression Calibration Method for Rotating Element Ellipsometers", Thin Solid Films, 234 (1993) is also disclosed as it describes a mathematical regression based approach to calibrating ellipsometer systems.

A paper by Nijs & Silfhout, titled "Systematic and Ramdom Errors in Rotating-Analyzer Ellipsometry", J. Opt. Soc. Am. A., Vol. 5, No. 6, (June 1988), describes a first order mathematical correction factor approach to accounting for window effects in Rotating Analyzer ellipsometers.

A paper by Kleim et al, titled "Systematic Errors in Rotating-Compensator ellipsometry", J. Opt. Soc. Am., Vol 11, No. 9, (September 1994) describes first order corrections for imperfections in windows and compensators in Rotating Compensator ellipsometers.

Other papers of interest in the area by Azzam & Bashara include one titled "Unified Analysis of Ellipsometry Errors Due to Imperfect Components Cell-Window Birefringence, and Incorrect Azimuth Angles", J. of the Opt. Soc. Am., Vol 61, No. 5, (May 1971); and one titled "Analysis of Systematic Errors in Rotating-Analyzer Ellipsometers", J. of the Opt. Soc. Am., Vol. 64, No. 11, (November 1974).

Another paper by Straaher et al, titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

A paper by Jones titled "A New Calculus For The Treatment Of Optical Systems", J.O.S.A., Vol. 31, (July 1941), is also identified as it describes the characterizing of multiple lens elements which separately demonstrate birefringence, as a single lens, (which can demonstrate reduced birefringence).

Finally, a paper which is co-authored by inventors herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol. 406, (1996) is also disclosed.

Even in view of the known art, especially in the context of ellipsometer and spectrophotometer systems, a need exists for a means to fashion a beam with a radially arbitrary intensity profile that does not quickly decay to zero, into a beam in which the intensity relatively directly radially approaches zero intensity.

DISCLOSURE OF THE INVENTION

The present invention comprises a functional equivalent to a Spatial Filter in the context of a system selected from the group:
  reflectometer;
  spectrophotometer;
  ellipsometer;
  spectroscopic ellipsometer;
  polarimeter; and
  spectroscopic polarimeter;
  and the like;

which system alone, or in combination with additional elements, generates an electromagnetic beam and causes it to impinge upon a sample system via said functional equivalent to said spatial filter;

which functional equivalent to a spatial filter serves to attenuate an outer annular region from said electromagnetic beam as it passes therethrough.

Said present invention method can be recited as, in the context of a selection from the group:
  reflectometer;
  spectrophotometer;
  ellipsometer;
  spectroscopic ellipsometer;
  polarimeter;
  spectroscopic polarimeter;
  and the like;

which alone or in combination with other elements causes a beam of electromagnetic radiation to interact with a sample system, comprising the steps of:
  a. providing a beam of electromagnetic radiation;
  b. providing a sample system;
  c. placing the equivalent to a spatial filter in the pathway of said electromagnetic beam such that said electromagnetic beam passes therethrough prior to said electromagnetic beam being caused to enter a detector;

the purpose being to eliminate a radially outer annulus of said electromagnetic beam which is comprised of a low intensity level irregular content.

In very general terms the present invention is a system which generates an electromagnetic beam and causes it to impinge upon a sample system, said system comprising, prior to said sample system an aperture, and said system comprising after the sample system a converging lens and a light fiber, said converging lens serving to image said aperture onto the input of said light fiber.

An important consideration of the present invention is that the optical fiber be of a small enough diameter to eliminate the outer annulus of the electromagnetic beam. An optical fiber nominal diameter is 50 microns, but said value can be more or less where function is not degraded.

Further, as the disclosed invention system operates spectroscopically, the converging lens is preferably constructed to affect various wavelengths similarly. Preferred lenses are then comprised of multiple elements, at least two of which are made from different materials, and specific examples thereof comprise two sequentially oriented elements, one of said two sequentially oriented elements being of a shape and orientation which individually converges a beam of electromagnetic radiation caused to pass therethrough, and the other being of a shape and orientation which individually diverges a beam of electromagnetic radiation caused to pass therethrough, wherein said convergence effect is greater than said divergence effect; there being a region between said at least two elements such that, in use, a beam of electromagnetic radiation sequentially passes through one of said at least two elements, then said region therebetween, and then the other of said at least two elements before emerging as an effectively converged, focused, beam of electromagnetic radiation. Said lens system can comprise a converging element selected from the group consisting of:
  a bi-convex;
  a plano-convex with an essentially flat side;

and wherein said diverging element presents as a selection from the group consisting of:
  a bi-concave lens element;
  a plano-concave with an essentially flat side;

said lens system comprising a selection from the group consisting of:
  a) a sequential combination of a bi-convex element and a bi-concave element;
  b) a sequential combination of a bi-concave element and a bi-convex element;
  c) a sequential combination of a bi-convex element and a plano-concave element with said concave side of said plano-concave element adjacent to said bi-convex element;

d) a sequential combination of a bi-convex element and a plano-concave element with said essentially flat side of said plano-concave element being adjacent to said bi-convex element;

e) a sequential combination of a plano-concave element and a bi-convex element with said essentially flat side of said plano-concave element adjacent to said bi-concave element;

f) a sequential combination of a plano-concave element and bi-convex element with said concave side of said plano-concave element adjacent to said bi-convex element;

g) a sequential combination of a plano-convex element and a bi-concave element with said essentially flat side of said plano-convex element adjacent to said bi-concave element;

h) a sequential combination of a biconcave element with a plano-convex element with said convex side of said plano-convex element adjacent to said biconcave element;

i) a sequential combination of a plano-concave element and a plano-convex element with the essentially flat side of said plano-concave element being adjacent to the convex side of the plano-convex element;

j) a sequential combination of a plano-concave element and a plano-convex element with the essentially flat side of said plano-concave element being adjacent to the convex side of said plano-convex element;

k) a sequential combination of a plano-convex element and a plano-concave element with the essentially flat side of said plano-covex element and the essentially flat side of said plano-concave element being adjacent to one another;

l) a sequential combination of a plano-concave element and a plano-convex element with the concave side of said plano-concave element being adjacent to the convex side of the plano-convex element;

m) a sequential combination of a plano-convex element and a bi-concave element with said convex side of said plano-convex element adjacent to said bi-concave element;

n) a sequential combination of a bi-concave element and a plano-convex element with said essentially flat side of said plano-convex element adjacent to said bi-concave element;

o) a sequential combination of a plano-convex element and a plano-concave element with said convex side of said plano-convex element adjacent to the concave side of the plano-concave element;

q) a sequential combination of a plano-concave element and a plano-convex element with said essentially flat side of said plano-convex element being adjacent to the essentially flat side of the plano-concave element;

r) a sequential combination of a plano-convex element and a plano-concave element with said convex side of said plano-convex element being adjacent to the essentially flat side of the plano-concave element;

s) a sequential combination of a plano-concave element with a plano-convex element with the essentially flat side of said plano-convex element being adjacent to the concave side of said plano-concave element;

and wherein said region between said at least two elements has essentially the optical properties of a selection from the group consisting of:
a void region; and
a functional equivalent to a void region.

The at least two elements can each be made of a material independently selected from the group consisting of:
$CaF_2$;
$BaF_2$;
$LiF$;
$MgF_2$; and
fused silica;

The present invention will be better understood by reference to the Detailed Description Section of this Specification, in conjunction with the Drawings.

SUMMARY OF THE INVENTION

It is a purpose and/or objective of the disclosed invention to teach application of a functional equivalent to a spatial filter in reflectometer, ellipsometer, spectroscopic ellipsometer, polarimeter, spectroscopic polarimeter, spectrophotometer and the like systems, to form a beam of electromagnetic radiation which presents with an intensity profile which drops off radially quickly to 0.0; said functional equivalent to a spatial filter comprising an aperture prior to a sample system, and a converging lens and optical fiber after said sample system.

It is a specific purpose and/or objective of the disclosed invention to teach in the context of reflectometer, ellipsometer, spectroscopic ellipsometer, polarimeter, spectroscopic polarimeter, spectrophotometer and the like systems, the positioning, prior to an investigated sample system, of an aperture, and after the sample system a converging lens and optical fiber, said components serving to form a functional equivalent to a spatial filter which fashion a beam of electromagnetic radiation which presents with an intensity profile which drops off radially quickly to 0.0.

It is a specific purpose and/or objective of the present invention to teach a method for forming a beam of electromagnetic radiation which presents with an intensity profile which drops off radially quickly to 0.0, in reflectometer, ellipsometer, spectroscopic ellipsometer, polarimeter, spectroscopic polarimeter, spectrophotometer and the like systems.

It is another purpose and/or objective of the disclosed invention to teach use of specific multiple element converging lenses which demonstrate spectroscopic characteristics.

Other purposes and/or objectives of the present invention will become apparent by a reading of the Specification and claims.

BRIEF DESCRIPTION OF THE DRAWINGS

FIG. 1a1 shows a basic Reflectometer or Spectrophotometer comprising a Source of Electromagnetic Radiation and a Detector.

FIGS. 1a2a, and 1a2b show demonstrative Ellipsometer systems in which components (AP) and (CL & OF) forming the present invention functional equivalent to a spatial filter system are shown positioned therein.

FIG. 1a3 shows construction of a quasi-achromatic multi-element lens which can be considered as present at AC1 or AC2 in FIG. 1a1.

FIG. 1a4 shows construction of a dual stage quasi-achromatic multi-element lens which can be considered as present at AC1 or AC2 in FIG. 1a1.

FIG. 1a5 shows a plot of spot diameter vs. wavelength which characterizes a dual stage quasi-achromatic multi-element lens as shown in FIG. 1a4, and of single stage fused silica and $CaF_2$ lenses.

FIG. 1*a*6 shows a plot of focal length vs. wavelength which characterizes a dual stage quasi-achromatic multi-element lens as shown in FIG. 1*a*4, and of single stage fused silica and CaF$_2$ lenses.

FIGS. 1*a*7–1*a*24 show various combinations of bi-concave, plano-concave, bi-convex and plano-convex lens elements which can comprise a present invention lens.

FIGS. 1*a*25–1*a*28 show various sequences of converging and diverging lens elements which can comprise a present invention dual lens system.

FIGS. 1*b*1–1*b*4 show, respectively, a positive miniscus lens; a negative miniscus lens; an aspheric convex lens and an aspheric concave lens.

FIG. 4 shows the effect of the presence of a spatial filter on the radial intensity of an electromagnetic beam as is developed and utilized in ellipsometer, reflectometer and spectrophotometer etc. systems.

DETAILED DESCRIPTION

Turning now to the Drawings, there is shown in FIG. 1*a*1 a basic Reflectometer or Spectrophotometer comprising a Source (LS) of Electromagnetic Radiation and a Detector (DET). A beam of electromagnetic radiation is shown reflecting from a Sample System (SS). Also shown is a present invention application of a functional equivalent to a Spatial Filter (SF), components of said Functional Equivalent to a Spatial Filter (SF) being shown and better presented and described with respect to FIG. 3*a*.

FIG. 1*a*2*a* shows a general elemental configuration of an ellipsometer system to which the present invention can be applied to investigate a material system (SS). Shown for reflection and transmission are:

a. a Source of a beam electromagnetic radiation (LS);
b. a Polarizer element (P);
c. optionally a compensator element (C1);
d. optional additional element(s) (AC1);
e. a sample system (SS);
f. optional additional element(s) (AC2);
g. optionally a compensator element (C2);
h. an Analyzer element (A); and
i. a Detector System (DET).

Figure 3A:
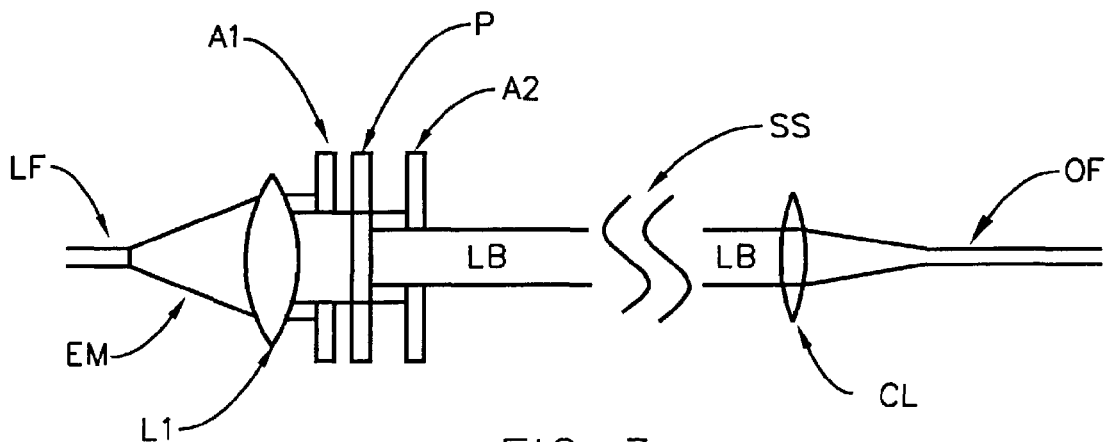
FIG. 3*a* shows an example of a the pre-sample present invention functional equivalent to a spatial filter of FIG. 2, in combination with the post-sample system location converging lens and optical fiber (eg. (CL) and (OF)).

The elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. optional "additional elements", (AC1) and (AC2), can be considered as being, for instance, components of the present invention functional equivalent to a spatial filter pre-sample system aperture (AP) and post-sample system converging lens and optical fiber (CL) and (OF), as shown in FIG. 3*a*.

Also note that after the Polarizer (P) there is indicated, in dashed lines, the presence of a present invention Functional Equivlent to a Spatial Filter Aperture (AP). While other pre-sample system locations, (eg. prior to the Polarizer (P), after the Compensator (C1) or after the Additional Elements (AC1), are included in the scope of the invention, the shown location is preferred.

Another embodiment of an ellipsometer system to which the present invention can be applied is shown in FIG. 1*a*2*b*, which shows a Perspective view of a demonstrative system. FIG. 1*a*2*b* shows a Light Source (LS) and a Polarizer (P), which in combination serve to produce a generally horizontally oriented Polarized Beam of Electromagnetic Radiation (LBI). Said generally horizontally oriented Polarized Beam of Electromagnetic Radiation (LBI) is caused to interact with Optical Element, (eg. Prism), (PRI), essentially totally internally reflect therein, pass through Focusing Optic (F1) and become generally vertically oriented Polarized Beam of Electromagnetic Radiation (LBI'), then interact with a Sample System (SS), which can be any Material System (MS), present on a Material System supporting Stage (STG). FIG. 1*a*2*b* shows that said interaction with the Surface of said Sample System (SS) causes a generally vertically oriented Polarized Beam of Electromagnetic Radiation (LBO') to pass through Focusing Optic (F2). FIG. 1*a*2*b* also shows that after passing through Focusing Optic (F2) said generally vertically oriented Polarized Beam of Electromagnetic Radiation (LBO') interacts with Optical Element, (eg. Prism), (PRO) and is essentially totally internally reflected thereby to become generally horizontally oriented Polarized Beam of Electromagnetic Radiation (LBO), which generally horizontally oriented Polarized Beam of Electromagnetic Radiation (LBO) passes through Analyzer (A) and then enters Detector System (DET), preferably via Circular Aperture (AP), for analysis. It is noted that the purpose of the Focusing Optics (F1) is to produce a very Concentrated High Intensity Small Area Polarized Beam of Electromagnetic Radiation (LBI') from Collimated Polarized Beam of Electromagnetic Radiation (LBI). The purpose of Focusing Optic (F2) is to "Re-Collimate" the generally vertically oriented Polarized Beam of Electromagnetic Radiation (LBO') which results from the Focused Polarized Beam of Electromagnetic Radiation (LBI') being Reflected from said Sample System (SS). The Re-Collimated generally vertically oriented Beam of Electromagnetic Radiation (LBI') being identified as generally horizontally oriented Beam of Electromagnetic Radiation (LBO) after it has been caused to interact with Prism (PRO).

Also, as in the FIG. 1*a*2*a* case, note that shown after the Polarizer (P) there is indicated, in dashed lines, the presence of a present invention Functional Equivalent to Spatial Filter Aperture (AP). Again, while other pre-sample system locations are included in the scope of the invention, the shown location is preferred. FIG. 1*a*2*b* also shows post-sample system present invention components (CL) and (OF) positioned in a preferred position. Note Said present invention components (CL) and (OF) could be positioned otherwise after the sample system (MS) and remain within the scope of the present invention.

FIG. 1*a*3 shows construction of a quasi-achromatic multi-element lens which can be considered as present at AC1 or AC2 in FIG. 1*a*1.

Figure 4:
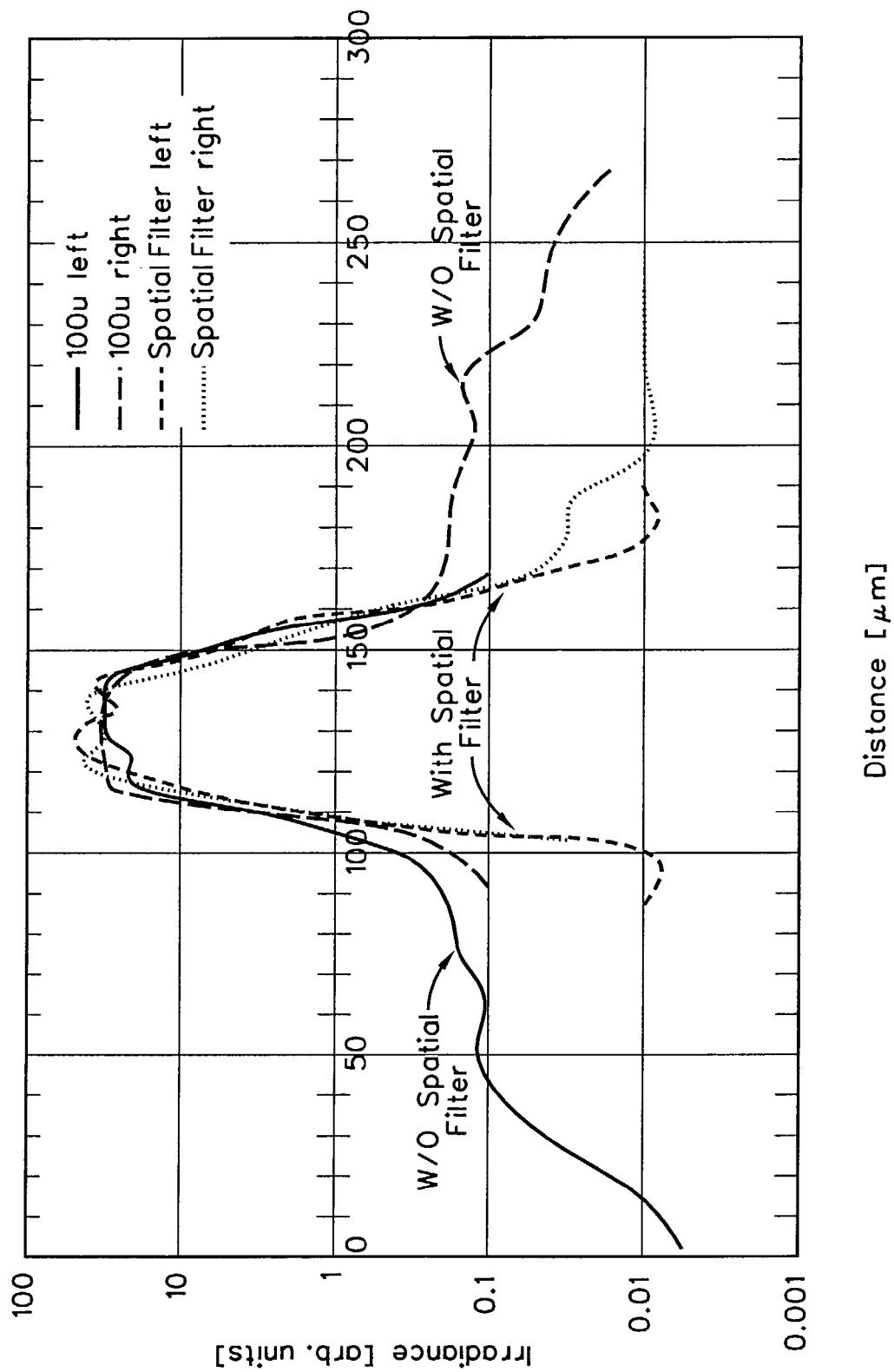

FIG. 1*a*4 shows the construction of a present invention dual quasi-achromatic multi-element lens which can be considered as present at AC1 or AC2, with an element sequence of:

((Diverging(D))(Converging(C))(Converging(C))(Diverging(D)));

as indicated in FIG. 1a28. In FIG. 1a4, it is to be understood that one, or both, of the two quasi-achromatic multi-element lens shown can be reversed left to right, (ie. replaced with a vertical mirror image), and remain within the scope of the present invention. Another embodiment provides that a sequence of lens elements be:

(Converging(C))(Diverging(D))(Converging(C))(Diverging(D));

as indicated in FIG. 1a25, which is achieved by providing a vertically oriented mirror image of the first lens system which is comprised of (FE1a) (FE2a) and (FE3a) in FIG. Ia4. Other arrangements are indicated in FIGS. 1a26 and 1a27:

(Converging(C))(Diverging(D))(Diverging(D))(Converging(C)); and (Diverging(D)) (Converging(C))(Diverging(D)) (Converging(C));

And, of course, other, (not shown), configurations within the scope of the present invention include:

(Converging(C))(Converging(C))(Diverging(D));
(Diverging(D))(Diverging(D))(Converging(C));
(Converging(C))(Diverging(D))(Diverging(D));
(Diverging(D))(Converging(C))(Diverging(D));
(Converging(C))(Converging(C))(Diverging(D))(Diverging(D)); and
(Diverging(D)) (Diverging(D)) (Converging(C)) (Converging(C)).

It should be appreciated that the additional elements in d. can then comprise selection(s) from the group consisting of:
beam directing means, (see (PRI) (PRO) in FIG. 1a2a);
input lens(es); and
window(s), as in a vacuum chamber;

and the additional elements in f. can then comprise selection(s) from the group consisting of:
beam directing means, (see (PRI) (PRO) in FIG. 1a2a);
output lens(es); and
window(s), as in a vacuum chamber.

As described with respect to FIG. 1a2b, at least one of the input and output lenses, (generally represented by (AC1) and (AC2) in FIG. 1a1), can, when selected and present, be of multi-element (FE1) (FE3) construction, wherein, for each of said input and output lenses (AC1) and (AC2), when selected and present, at least two elements (FE1) and (FE3) thereof are made from different materials, such that in use the focal length for each wavelength in a range of wavelengths is essentially the same as that for every other wavelength, wherein at least one of said input and output lenses, when selected and present, demonstrates properties selected from the group consisting of:
both demonstrating birefringence;
neither demonstrating birefringence;
one demonstrating birefringence and the other not.

Representative materials from which different elements in said input and output lenses can be made are calcium fluoride (FE1) (FE1a) (FE1b), and fused silica (FE3), (FE3a) (FE3b). In more detail FIGS. 1a7–1a24 show, respectively:

a) a sequential combination of a bi-convex element and a bi-concave element;

b) a sequential combination of a bi-concave element and a bi-convex element;

c) a sequential combination of a bi-convex element and a plano-concave element with said concave side of said plano-concave element adjacent to said bi-convex element;

d) a sequential combination of a bi-convex element and a plano-concave element with said essentially flat side of said plano-concave element being adjacent to said bi-convex element;

e) a sequential combination of a plano-concave element and a bi-convex element with said essentially flat side of said plano-concave element adjacent to said bi-concave element;

f) a sequential combination of a plano-concave element and bi-convex element with said concave side of said plano-concave element adjacent to said bi-convex element;

g) a sequential combination of a plano-convex element and a bi-concave element with said essentially flat side of said plano-convex element adjacent to said bi-concave element;

h) a sequential combination of a bi-concave element with a plano-convex element with said convex side of said plano-convex element adjacent to said bi-concave element;

i) a sequential combination of a plano-concave element and a plano-convex element with the essentially flat side of said plano-concave element being adjacent to the convex side of the plano-convex element;

j) a sequential combination of a plano-concave element and a plano-convex element with the essentially flat side of said plano-concave element being adjacent to the convex side of said plano-convex element;

k) a sequential combination of a plano-convex element and a plano-concave element with the essentially flat side of said plano-covex element and the essentially flat side of said plano-concave element being adjacent to one another;

l) a sequential combination of a plano-concave element and a plano-convex element with the concave side of said plano-concave element being adjacent to the convex side of the plano-convex element;

m) a sequential combination of a plano-convex element and a bi-concave element with said convex side of said plano-convex element adjacent to said biconcave element;

n) a sequential combination of a bi-concave element and a plano-convex element with said essentially flat side of said plano-convex element adjacent to said bi-concave element;

o) a sequential combination of a plano-convex element and a plano-concave element with said convex side of said plano-convex element adjacent to the concave side of the plano-concave element;

q) a sequential combination of a plano-concave element and a plano-convex element with said essentially flat side of said plano-convex element being adjacent to the essentially flat side of the plano-concave element;

r) a sequential combination of a plano-convex element and a plano-concave element with said convex side of said plano-convex element being adjacent to the essentially flat side of the plano-concave element;

s) a sequential combination of a plano-concave element with a plano-convex element with the essentially flat side of said plano-convex element being adjacent to the concave side of said plano-concave element;

FIGS. 1b1–1b4 show, respectively, a positive miniscus lens; a negative miniscus lens; an aspheric convex lens and an aspheric concave lens. Said lens types can be utilized in the present invention at AC1 and/or AC2 and/or AC2' in FIG. 1a1; and at F1 and/or F2 in FIG. 1a2 in addition to or instead of lens configurations shown in FIGS. 1a2b, 1a4 and 1a7–1a24.

It is noted that (PRI) and (PRO) can be made of the same material, but the preferred embodiment provides that (PRI) be made of BK7 (refractive index approximately 1.55) and that (PRO) be made of F2 (refractive index approximately 1.7).

Figure 2:
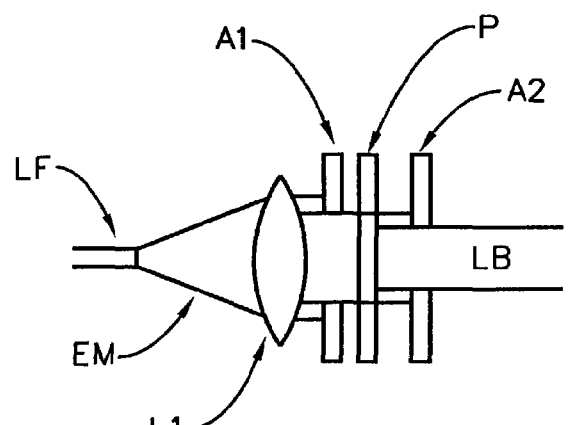
FIG. 2 shows an example of a source of electromagnetic radiation comprising a light fiber, a lens, apertures and polarizer. The apertures (A1) and primarily (A2), form the pre-sample system portion of the functional equivalent to a spatial filter.

FIG. 2 shows that a Light Source (LS) can comprise a Light Fiber, a Lens (L1), and a First Aperture (A1). In the context of an ellipsometer a Polarizer (P) is also shown as it would be positioned. Shown in addition is a second Aperture (A2). In use electromagnetic radiation (EM) exiting the Light Fiber (LF) expands and enters Lens (L1) and is collimated thereby. First Aperture (A1) limits the beam diameter, and Second Aperture (A2) further does so to provide a beam of electromagnetic radiation labeled (LB). Apertures (A2), in particular, corresponds to Aperture (AP) of the present invention as shown in 1a2a and 1a2b.

FIG. 3a expands on FIG. 2 and shows a present invention functional equivalent to a spatial filter configuration. The present invention Apertures (A1) and particularly (A2) are placed so as to intercept the beam of electromagnetic radiation labeled (LB). Particularly aperture (A2) is the present invention Aperture (AP) shown in FIGS. 1a1 and 1a2a. FIG. 3a implies electromagnetic beam interaction with a sample system, and further shows present invention functional equivalent to a spatial filter converging lens (CL) and optical fiber (OF) components. Note that the converging lens (CL) effectively focuses the image of Aperture (A2) onto the input to the Optical Fiber (OF).

Figure 3B:
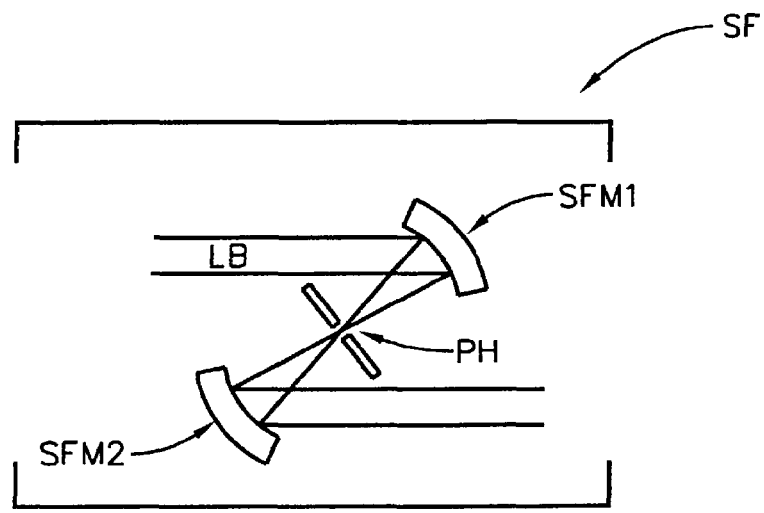
FIG. 3*b* demonstrates a spatial filter (SF) per se.
Figure 3C:
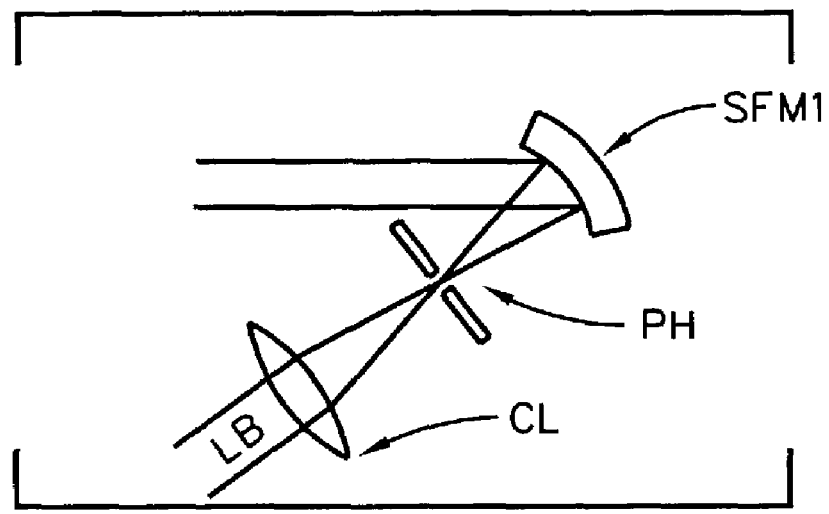
FIG. 3*c* demonstrates an alternative spatial filter (SF) per se.

FIG. 3b is included to show a demonstrative per se. Spatial Filter (SF), which the present invention functionally emulates via the coordinated effects of the FIG. 3a pre-sample system Aperture (A2), and the post-sample system Converging Lens (CL) and Optical Fiber (OF). Indicated are a beam of electromagnetic radiation (LB) which reflects from converging mirror (SFM1), through the Pin Hole (PH), then reflects from re-collimating mirror (SFM2). Note that at least one reflecting mirror ((SFM1) or (SFM2)) can be replaced with transmissive Lenses, and FIG. 3c is included to show a demonstrative per se. Spatial Filter (SF), which the present invention functionally emulates via the coordinated effects of the FIG. 3a pre-sample system Aperture (A2), and the post-sample system Converging Lens (CL) and Optical Fiber (OF). Indicated are a beam of electromagnetic radiation (LB) which is focused by converging lens (CL) through the Pin Hole (PH), and which then reflects from re-collimating mirror (SFM1).

FIG. 3c demonstrates a spatial filter comprised of a lens (CL) and reflective mirror (SFM1). Note that the electromagetnic beam (LB) can be entered as shown to the lens (CL), or can be entered to the reflective mirror (SFM1).

Figure 3D:
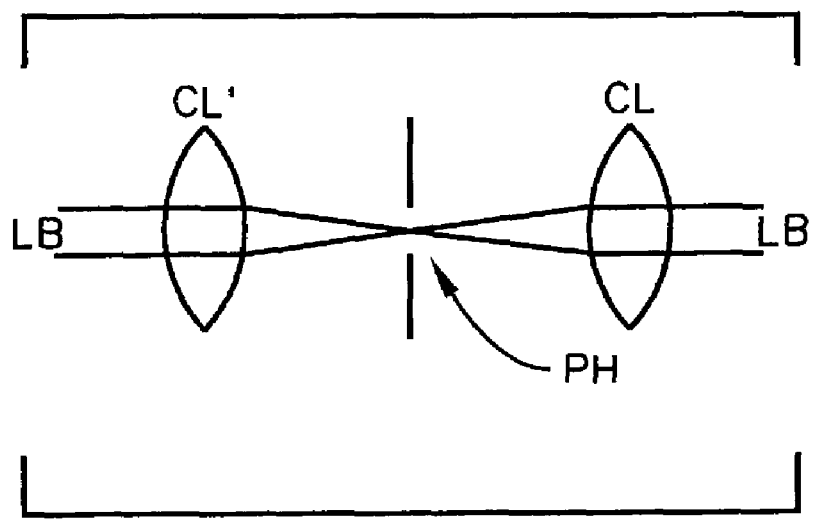
FIG. 3*d* demonstrates an alternative spatial filter (SF) per se.

FIG. 3d shows another demonstrative spatial filter comprised of two Lenese (CL) which have a Pin Hole at their Focal Points.

The Spatial Filters in FIGS. 3b–3d can further have a converging lens added and positioned to focus the output beam onto the input of a an optical fiber, as demonstrated in FIG. 3a.

FIG. 4 shows the effect of the presence of a Spatial Filter (SF) on the Intensity Profile of a beam of electromagnetic radiation passed therethrough. Note that FIG. 4 plots Intensity on a Log Axis, and that the Intensity drops toward 0.001 much quicker when the Spatial Filter (SF) is in place than when it is not in place.

The present invention also includes, in the context of a reflectometer, a spectrophotometer, an ellipsometer, a spectroscopic ellipsometer, a polarimeter, a spectroscopic polarimeter, and a spectrophotometer and the like systems, the Method of removing an radial outer annular ring from an electromagnetic beam by application of a spatial filter prior to a Sample System. Said method can be recited as a method of processing source electromagnetic beams to eliminate a radially outer annulus thereof, said radial outer annulus often being comprised of low intensity level irregular content, said method comprising placing the present invention functional equivalent to spatial filter(s) such that said electromagnetic beam passes therethrough.

The terminology "outer annular region" as used herein is to be interpreted to mean an outer region of an electromagnetic beam, as distinct from a central region thereof, which outer region appears as an annulus when it is considered that the intensity of the beam decreases to zero as the radius increases to infinity. Said "outer annular region" can be considered to begin at the point where the intensity of an electromagnetic beam falls to where intensity becomes irregular rather than continues directly to zero. This often occurs at below approximately ten (10%) percent of maximum intensity, and it is noted, can contain approximately two (2%) to five (5%) of the electromagnetic beam's energy content.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

We claim:

1. A system comprising a functional equivalent to a spatial filter which serves to attenuate an outer annular region from said electromagnetic beam as it passes therethrough;

said functional equivalent to a spatial filter being present in the context of a system comprising:

means for generating an electromagnetic beam;

means for causing it to impinge upon a sample system, and means for detecting said electromagnetic beam after it interacts with said sample system;

said functional equivalent to a spatial filter comprising an aperture prior to said sample system, and after the sample system a converging lens and a light fiber, said converging lens serving to image said aperture onto the input of said light fiber;

such that in use the central portion of the electromagnetic beam which is caused to pass through said aperture, becomes focused on the input to said optical fiber by said converging lens after interaction with said sample system, and said optical fiber conveys said central portion of the electromagnetic beam to said means for detecting said electromagnetic beam after it interacts with said sample system;

wherein said system is distinguished in that said converging lens is characterized by a selection from the group consisting of:

a) said converging lens comprises at least two sequentially oriented elements, one of which is made of made of a material selected from the group consisting of:
$CaF_2$;
$BaF_2$;
LiF; and
$MgF_2$;
and another of said at least two sequentially oriented elements in said input lens is made of fused silica; and
b) said converging lens comprises a selection from the group consisting of:
a positive miniscus lens; and
an asymetric convex lens.

2. A system as in claim 1 wherein the system is selected from the group consisting of:
reflectometer;
spectrophotometer;
ellipsometer;
spectroscopic ellipsometer;
polarimeter; and
spectroscopic polarimeter.

3. A system as in claim 1, in which the system comprises:
polarization state generator which functionally includes said aperture; and
polarization state detector which functionally includes said focusing lens and an optical fiber.

4. A system as in claim as in claim 1 wherein the optical fiber has a diameter of 50 microns or less.

5. A system as in claim in claim 1, characterized by at least one condition selected from the group consisting of:
a. said converging lens comprises at least two sequentially oriented elements, and is characterized by being a selection from the group consisting of:
a sequential combination of a converging element and a diverging element;
a sequential combination of a diverging element and a converging element;
a sequential combination of a converging element, a diverging element, a converging element and a diverging element;
a sequential combination of a converging element, a diverging element, a diverging element and a converging element;
a sequential combination of a diverging element, a converging element, a diverging element and a converging element;
a sequential combination of a diverging element, a converging element, a converging element and a diverging element;
a sequential combination of at least two elements, one of which is a miniscus lens; and
a sequential combination of at least two elements, one of which is an aspherical lens;
b. said converging lens comprises at least two sequentially oriented elements with a region between at least two of said at least two elements is characterized as a selection from the group consisting of:
a void region; and
a functional equivalent to a void region.

6. A method of processing electromagnetic beams to eliminate a radially outer annulus thereof, said method comprising placing an equivalent to a spatial filter such that said electromagnetic beam passes therethrough, said functional equivalent to a spatial filter sequentially comprising:
an aperture;
a focusing lens;
an optical fiber;
said focusing lens being characterized by a selection from the group consisting of:
a) said focusing lens comprises at least two sequentially oriented elements, one of which is made of made of a material selected from the group consisting of:
$CaF_2$;
$BaF_2$;
LiF; and
$MgF_2$;
and another of said at least two sequentially oriented elements in said input lens is made of fused silica; and
b) said focusing lens comprises a selection from the group consisting of:
a positive miniscus lens; and
an asymetric convex lens;
such that in use the electromagnetic beam is caused to at least partially pass through said aperture, interact with a sample system, and then become focused by said focusing lens and enter said optical fiber.

7. A method of investigating a sample system, in the context of a selection from the group consisting of:
reflectometer;
spectrophotometer;
ellipsometer;
spectroscopic ellipsometer;
polarimeter; and
spectroscopic polarimeter;
which causes a beam of electromagnetic radiation to interact with a sample system;
comprising the steps of:
a. providing a beam of electromagnetic radiation;
b. providing a sample system;
c. placing an aperture in the pathway of said electromagnetic beam such that said electromagnetic beam at least partially passes therethrough prior to said electromagnetic beam being caused to interact with said sample system and placing a focusing lens and optical fiber after said sample;
said focusing lens being characterized by a selection from the group consisting of:
a) said focusing lens comprises at least two sequentially oriented elements, one of which is made of made of a material selected from the group consisting of:
$CaF_2$;
$BaF_2$;
LiF; and
$MgF_2$;
and another of said at least two sequentially oriented elements in said input lens is made of fused silica; and
b) said focusing lens comprises a selection from the group consisting of:
a positive miniscus lens; and
an asymetric convex lens;
such that in use the electromagnetic beam is caused to at least partially pass through said aperture, interact with a sample system, and then become focused by said focusing lens and enter said optical fiber;
the purpose being to eliminate a radially outer annulus of said electromagnetic beam which is comprised of a low intensity level irregular content.

* * * * *